(12) United States Patent
Simi et al.

(10) Patent No.: US 12,708,473 B2
(45) Date of Patent: Aug. 18, 2026

(54) TIP PROTECTOR FOR A SURGICAL INSTRUMENT, ASSEMBLY AND METHOD

(71) Applicant: MEDICAL MICROINSTRUMENTS, INC., Pisa (IT)

(72) Inventors: Massimiliano Simi, Pisa (IT); Giorgio Lazzari, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 641 days.

(21) Appl. No.: 17/760,465

(22) PCT Filed: Feb. 9, 2021

(86) PCT No.: PCT/IB2021/051025
§ 371 (c)(1),
(2) Date: Aug. 10, 2022

(87) PCT Pub. No.: WO2021/161159
PCT Pub. Date: Aug. 19, 2021

(65) Prior Publication Data

US 2023/0144183 A1 May 11, 2023

(30) Foreign Application Priority Data

Feb. 10, 2020 (IT) ........................ 102020000002551

(51) Int. Cl.
*A61B 90/00* (2016.01)
*A61B 17/00* (2006.01)
*A61B 17/29* (2006.01)

(52) U.S. Cl.
CPC .... *A61B 90/03* (2016.02); *A61B 2017/00477* (2013.01); *A61B 2017/00862* (2013.01);
(Continued)

(58) Field of Classification Search
CPC .................... A61B 90/03; A61B 90/08; A61B 2017/00477; A61B 2017/00862;
(Continued)

(56) References Cited

U.S. PATENT DOCUMENTS 5,725,536 A * 3/1998 Oberlin ............ A61B 17/07207 606/139
5,820,009 A * 10/1998 Melling ........... A61B 17/07207 227/176.1
(Continued)

FOREIGN PATENT DOCUMENTS

EP 2567662 A1 3/2013
EP 3243449 A2 11/2017
(Continued)

OTHER PUBLICATIONS

International Search Report and Written Opinion for International Patent Application No. PCT/IB2021/051025, mailed Apr. 30, 2021, 11 pp.

*Primary Examiner* — Tan-Uyen T Ho
*Assistant Examiner* — Osama Nemer
(74) *Attorney, Agent, or Firm* — Armstrong Teasdale LLP

(57) ABSTRACT

A tip protector, for a surgical instrument having a shaft and an instrument tip near a distal portion of the shaft, includes a tip housing for releasably receiving the instrument tip; a clamp system suitable for gripping a portion of the surgical instrument to position the tip protector; and a distal through opening at or near the distal end of the tip housing. The distal through opening has an opening size that is adjustable.

22 Claims, 9 Drawing Sheets

(52) U.S. Cl.
CPC ................ *A61B 2017/2927* (2013.01); *A61B 2017/2939* (2013.01); *A61B 2090/034* (2016.02); *A61B 2090/08021* (2016.02)

(58) Field of Classification Search
CPC .... A61B 2017/2927; A61B 2017/2939; A61B 2017/00336; A61B 2090/034; A61B 2090/08021; A61B 2090/033; A61B 2090/0801; A61B 17/3496; A61B 34/37
See application file for complete search history.

(56) References Cited

U.S. PATENT DOCUMENTS

| | | | | |
|---|---|---|---|---|
| 10,285,695 | B2 * | 5/2019 | Jaworek | A61B 17/07207 |
| 10,335,196 | B2 * | 7/2019 | Hess | A61B 17/3496 |
| 10,582,975 | B2 | 3/2020 | Simi et al. | |
| 10,864,051 | B2 | 12/2020 | Simi et al. | |
| 2006/0079884 | A1 * | 4/2006 | Manzo | A61B 34/37 606/41 |
| 2014/0276949 | A1 | 9/2014 | Staunton et al. | |
| 2016/0213434 | A1 * | 7/2016 | Lohmeier | A61B 17/00234 |
| 2017/0007254 | A1 * | 1/2017 | Jaworek | A61B 17/320068 |
| 2017/0224191 | A1 | 8/2017 | Ramsey | |
| 2019/0313889 | A1 | 10/2019 | Wassenburg et al. | |

FOREIGN PATENT DOCUMENTS

| | | | |
|---|---|---|---|
| EP | 3556315 | A1 | 10/2019 |
| NO | 2019220408 | A1 | 11/2019 |
| WO | 2017064303 | A1 | 4/2017 |
| WO | 2017064306 | A1 | 4/2017 |
| WO | 2018189721 | A1 | 10/2018 |
| WO | 2018189722 | A1 | 10/2018 |
| WO | 2019220407 | A1 | 11/2019 |
| WO | 2019220409 | A1 | 11/2019 |

* cited by examiner

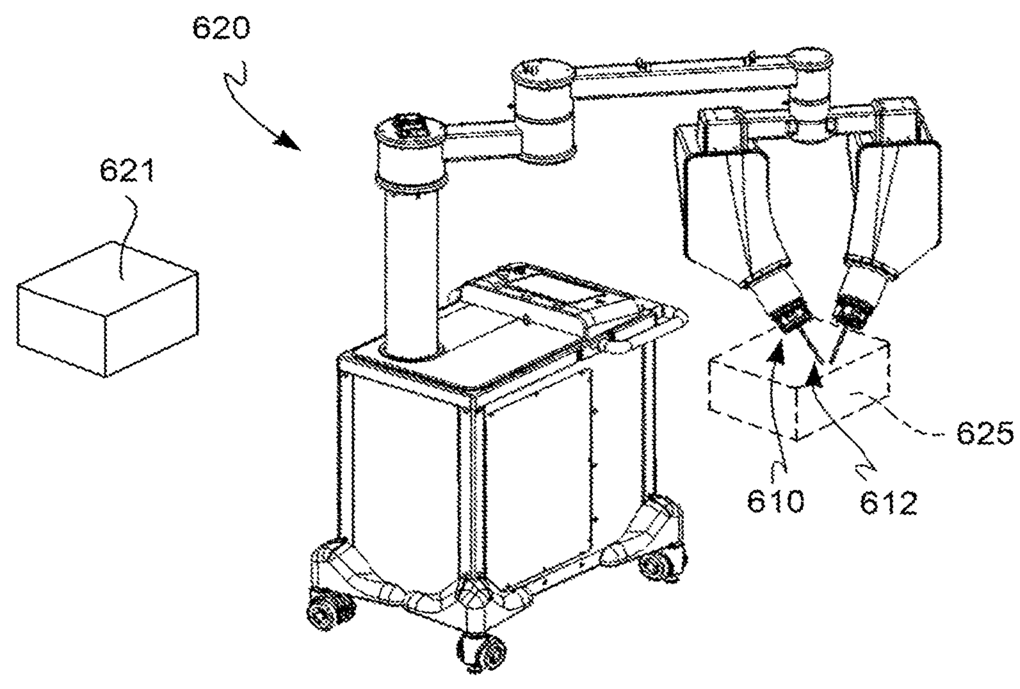
FIG.1
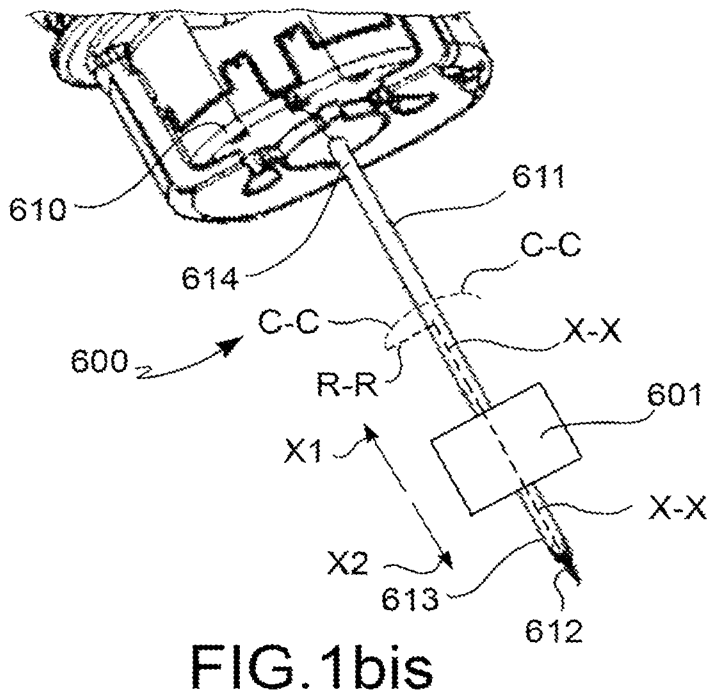
FIG.1bis

TIP PROTECTOR FOR A SURGICAL INSTRUMENT, ASSEMBLY AND METHOD

CROSS-REFERENCE TO RELATED APPLICATIONS

This application is a National Stage Application of International Patent Application No. PCT/IB2021/051025, having an International Filing Date of Feb. 9, 2021, which claims priority to Italian Application No. 102020000002551, filed Feb. 10, 2020, each of which is hereby incorporated by reference in its entirety.

FIELD OF THE INVENTION

It is an object of the present invention to disclose a tip protector.

In particular, the present invention relates to a tip protector for a surgical instrument.

The present invention also relates to an assembly of tip protector and surgical instrument.

Furthermore, the present invention relates to a method.

BACKGROUND

Robotic surgery apparatuses are generally known in the art and typically comprise a master console, a robotic central tower (or robotic cart) and a plurality of robotic arms extending from the central tower, an example of which is disclosed in document U.S. Ser. No. 10/864,051 of the same Applicant. Each robotic arm typically comprises a teleoperated robotic motorized positioning system (or manipulator) for moving a slave surgical instrument distally attached thereto, in order to position said surgical instrument so that it can reach an operatory volume of the patient anatomy. Documents WO-2019-220407, WO-2019-220408 and WO-2019-220409 in the name of the same Applicant disclose several embodiments of master-slave robotic surgery system having a mechanically unconstrained, mechanically ungrounded master input tool designed to be hand-held by the surgeon in a predefined volume in order to actuate the slave surgical instrument.

The slave surgical instrument typically comprises an elongated shaft having at the distal end an articulated or jointed tip designed for operating a patient and usually comprising a metallic distal pointed end and/or a sharp blade for piercing and/or cutting a patient's tissue. The motorized robotic positioning system is therefore designed to position the tip of at least one surgical instrument at or near an operatory volume of the patient anatomy. Known cable driven motorized positioning systems typically include a set of motorized capstans or pulleys able to wind and unwind the cable for actuating a degree of freedom of the surgical instrument, for example the grip degree of freedom of the instrument tip.

After having positioned the tip at or near an operatory volume of the patient anatomy, the motorized robotic positioning system typically freezes, and the articulated device provides the desired degrees of freedom of motion to the tip. Documents U.S. Ser. No. 10/582,975, WO-2017-064303, WO-2017-064306, WO-2018-189721 and WO-2018-189722 in the name of the same Applicant disclose several embodiments of slave surgical instruments for robotic surgery having a pitch-yaw-grip distal articulated tip.

Slave surgical instruments having a flexible robotic arm proximal to the instrument tip are also known in the field.

Several surgical procedures, such as sutures, the execution of blood vessel anastomosis comprising small diameter vessels and nerves, the reconstruction of anatomic parts after the occurrence of traumatic lesions, in re-vascularization of tissues, reattachment of limbs, transplantation and replantation procedures, may be carried out by virtue of known slave surgical instruments.

The articulated tip of known slave surgical instruments are delicate and fragile components, because of the high technological content, and the fragility normally increases as the size of the tip miniaturizes.

At least for the reasons set forth above, it is strongly felt the need of protecting the tip of a slave surgical instruments for robotic surgery.

Known solutions to protect the tip of a slave surgical instrument include caps or cages fitting onto the distal tip thereof. The action of protecting a pointed tip or a sharp-trimmed blade prevents direct collisions of the tip against a hard object within the operatory field, thereby preventing damages to the tip, and thus allows the use of the same surgical instrument for several surgeries, after proper sterilization. Moreover, the action of protecting a pointed tip or a sharp-trimmed blade reduces the risk of unwanted damages to healthy organs, for example that can occur due to poor control over a robotic manipulation of the slave surgical instrument while approaching the patient's anatomy.

In particular, robotic-aided laparoscopy requires the slave surgical instrument to penetrate beneath the body skin through a set of pre-positioned surgical access in form of hollow trocars across the patient's skin. It is therefore critical that the slave surgical instrument tip is protected by a cap before its insertion into the hollow trocar. Known solutions designed for protecting the tip of a laparoscopic surgical instrument are shown in document US-2017-0224191, which shows a "V"-shaped tip cap having a distal cap shield, two flexible arms extending backwards from the cap shield and carrying each a collar portion made of a half-pipe for receiving the tip of the laparoscopic surgical instrument, a latching closure at the opposite end of the arms. A plurality of through holes are provided for drainage of liquids from the tip cap. An abutment stop element impedes the tip of the laparoscopic instrument to protrude from the tip cap.

Other known examples of tip protectors for laparoscopic surgical instruments are disclosed by US-2019-0313889, and in particular this document shows an embodiment of tip cap having a clamp device for attaching to the tip, a blocking device for locking in a predefined configuration the parts of the clamp device, and a plurality of through holes for drainage. In one embodiment the clamp device is made of two parts hinged to one another near the distal end of the tip cap. In addition, document US-2016-0213434 shows a further known example of tip protector.

In the field of microsurgery, robotic apparatuses allow a higher degree of miniaturization of the surgical instrument when compared to traditional microsurgery and allows at the same time to reduce the transmission of hand tremor to the slave surgical instrument of the robotic surgery system.

Some applications of robotic-aided microsurgery desire the presence of the surgeon within the sterile operatory arena during the robotic-aided surgery so that during a single intervention, the same micro-surgeon switches from robotic-aided microsurgery to traditional (non-robotic) microsurgery and vice versa. Thereby, the slave surgical instrument of the robotic micro-surgical system may be not in use for the whole duration of the surgery, and in particular the use of the robotic surgical instrument may be suspended for a while during a same surgery and then restored.

An example of cap for protecting a needle that is retractable along the instrument shaft is disclosed in document EP-2567662.

There is a need to expose the tip of the surgical instrument without having to move the instrument away from the operative volume of the patient's anatomy or having to reposition the surgical instrument within the operative volume of the patient's anatomy.

It is therefore strongly felt the need of protecting the tip of a surgical instrument while the surgical instrument is positioned at or near an operatory volume of a patient anatomy.

Solution

It is a scope of the present invention to overcome the drawbacks cited within the prior art references.

According to an aspect of the devices, assemblies, and methods disclosed, a tip protector is provided for a surgical instrument having a shaft and an articulated instrument tip at a distal portion of the shaft, wherein the tip protector comprises a tip housing for releasably receiving the instrument tip, a clamp system, suitable for gripping a portion of the surgical instrument to position the tip protector, a distal through opening at or near the distal end of the tip housing.

The distal through opening may have an opening size that is adjustable so that said distal through opening can be adjusted in such way to become a through opening for at least the instrument tip, thereby making the tip protector repositionable at various location along the shaft of the surgical instrument.

The locations along the shaft may comprise features for holding in place the tip protector.

The distal opening of the tip protector may be elastically adjustable.

The tip protector may comprise one or more abutment surfaces for constraining at least some of the degrees of freedom of the articulated instrument tip in a predefined configuration. For example, the predefined configuration is a straight configuration of the articulated instrument tip aligned to the shaft.

A method for constraining an articulated instrument tip may comprise the steps of positioning and/or repositioning a tip protector having a tip housing comprising at least one tip abutment surface on the articulated instrument tip so that at least one tip abutment surface of the tip protector abuts against the instrument tip from opposite sides of the articulated instrument tip, exerting a constraining action on the articulated instrument tip, blocking at least one degree of freedom of the articulated instrument tip.

Thanks to the proposed solutions, it is allowed to selectively expose the articulated tip of a surgical instrument when the surgical instrument is within an operatory volume near or within a patient's anatomy as well as to protect the same tip of the surgical instrument when the surgical instrument is within the same operatory volume.

Thanks to the repositionable tip protector, protection and exposure of the tip is made faster and do not require repositioning of the surgical instrument within the operatory volume.

Thanks to the proposed solutions, it is allowed to transfer any mechanical load from the tip protector to the shaft, thereby protecting the instrument tip from any overloading actions.

Thanks to the proposed solution it is possible to constrain at least some of the degrees of freedom of the instrument tip in a predefined configuration.

FIGURES

Further characteristics and advantages of the tip protector, the assembly, the system and the method will appear from the description reported below of preferred embodiments, which are given as examples and are not meant to be limiting, which makes reference to the attached figures, in which:

FIG. 1 is an axonometric view showing diagrammatically a robotic surgery system, according to an embodiment;

FIG. 1*bis* is an axonometric view showing diagrammatically an assembly of tip protector and surgical instrument, according to an embodiment;

FIGS. 2, 3 and 4 are elevation side view showing diagrammatically an assembly of tip protector and surgical instrument in different configurations, according to an embodiment, as well as some steps of a method according to a possible mode of operation, wherein FIG. 2 shows a partial cross-section for sake of clarity;

Figure 16:
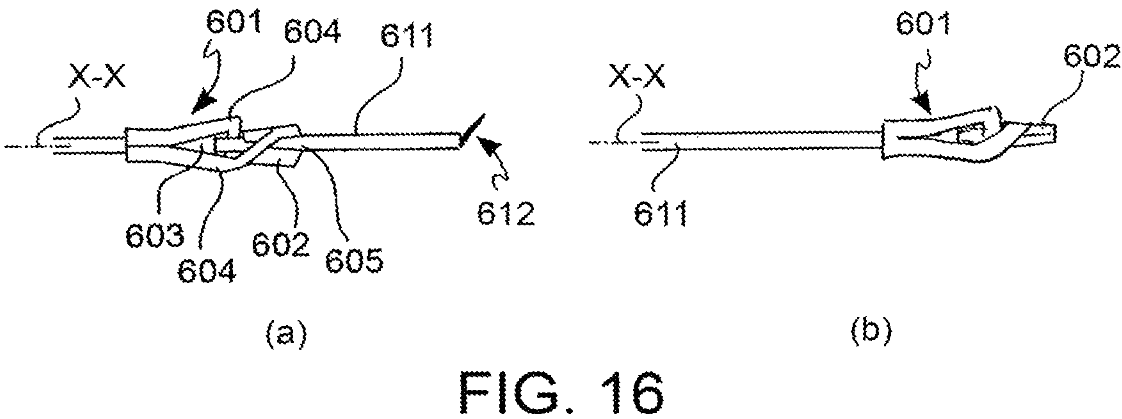
Figure 17:
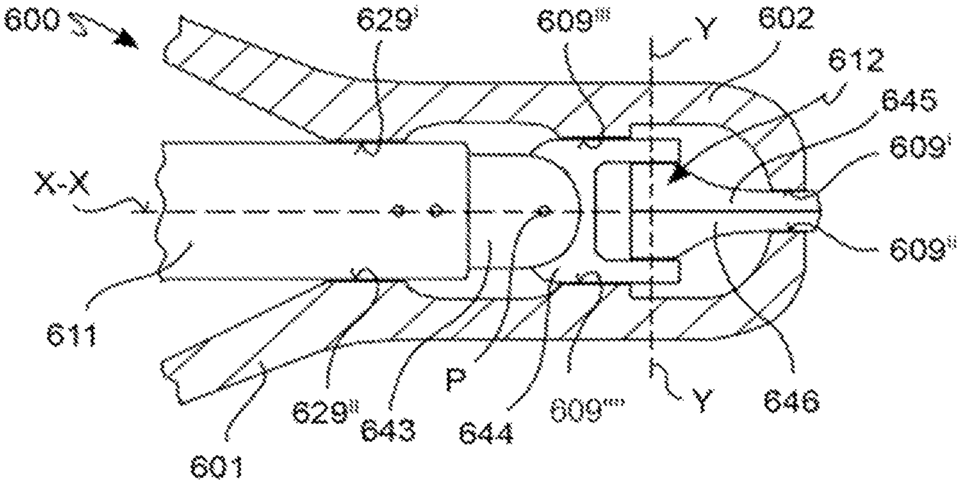
Figure 18:
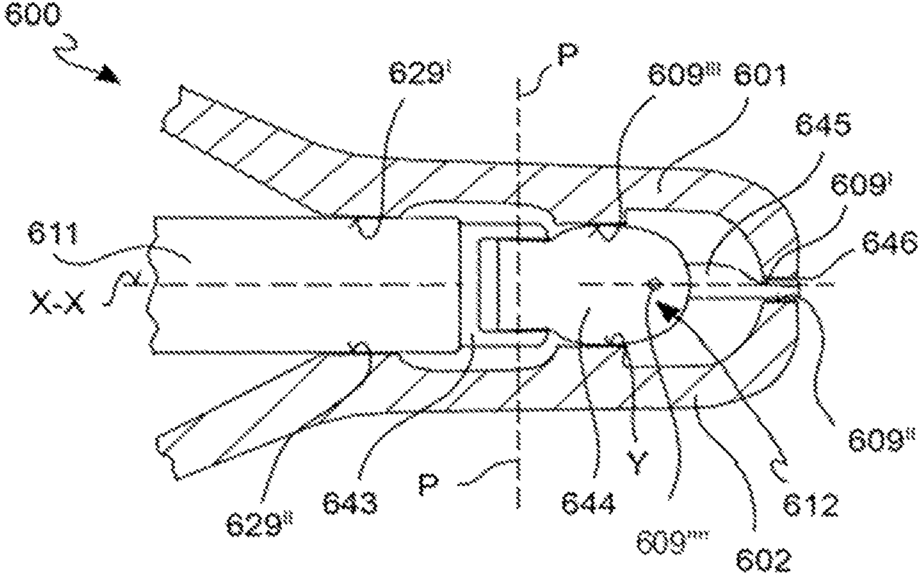

FIG. 16 (*a*)-(*b*) shows diagrammatically an assembly of tip protector and surgical instrument in different configurations, according to an embodiment;

FIG. 17 is a diagrammatic cross-section along the longitudinal direction showing a tip protector covering an instrument tip, according to an embodiment;

FIG. 18 is a diagrammatic cross-section along the longitudinal direction showing a tip protector covering an instrument tip, according to an embodiment.

DETAILED DESCRIPTION OF SOME EMBODIMENTS

According to a general embodiment, it is provided a tip protector 601 for a surgical instrument 610. The surgical instrument 610 has a shaft 611 extending along a longitudinal direction X-X and an articulated instrument tip 612 at a distal portion 613 of the shaft 611.

The tip protector 601 comprises a tip housing 602 for releasably receiving the articulated instrument tip 612, a clamp system 603, suitable for gripping a portion of the shaft 611 to position the tip protector 601, and a distal through opening 605 at or near the distal end 690 of the tip housing 602.

Said distal through opening 605 has an opening size 606 that is adjustable so that said distal through opening 605 can be adjusted in such way to become a through opening for at least the instrument tip 612, thereby making the tip protector 601 repositionable at various locations along the shaft 611.

Preferably, said tip housing 602 comprises at least one tip abutment surface 609', 609", 609'", 609"" suitable for abutting against the instrument tip 612 from opposite sides thereof for exerting a constraining action on the instrument tip 612 at least in a direction which is transversal to the longitudinal direction X-X of the shaft 611, with the purpose to block at least one of the degrees of freedom of said articulated instrument tip 612.

Thereby, when the articulated tip 612 is housed within the cavity of the tip housing 602, said at least one abutment surface 609', 609", 609'", 609"" abuts against the articulated tip 612 from opposite sides of the tip 612, exerting a constraining action on the articulated tip 612, said constraining action blocks at least one degree of freedom of the articulated tip 612.

The articulated tip 612 may have also one or more translational degrees of freedom blocked by the tip protector 601 when the articulated tip 612 is received within said housing 602.

According to a preferred embodiment, said at least one tip abutment surface 609', 609", 609'", 609"" is suitable to block each and all the degrees of freedom of said articulated instrument tip 612. Thereby, when the articulated tip 612 is housed within the cavity of the tip housing 602, said at least one abutment surface 609', 609", 609'", 609"" abuts against the articulated tip 612 from opposite sides of the tip 612, exerting a constraining action on the articulated tip 612, said constraining action blocks each and all the degrees of freedom of the articulated tip 612, for example the degrees of freedom of pitch P, yaw Y and grip G.

Preferably, said constraining action is suitable for blocking at least one of the degrees of freedom of said articulated instrument tip 612 even when said at least one of the degrees of freedom is actuated. When said constraining action blocks each and all the degrees of freedom of the articulated tip 612, said constraining action blocks each and all the degrees of freedom even when said at least one of the degrees of freedom is actuated.

According to a preferred embodiment, the tip protector 601 comprises one or more further abutment surfaces 629', 629", also called shaft abutting surfaces 629', 629", suitable for abutting against the instrument shaft 611 of the surgical instrument 610, with the purpose of acting as a reference for exerting said constraining action on the articulated instrument tip 612.

According to a preferred embodiment, said at least one tip abutment surface 609', 609", 609'", 609"" is connected to at least one elastic element so that said constraining action is an elastic constraining action, and preferably said elastic constraining action is an auto-centering [i.e.: self-centering] constraining action.

According to a preferred embodiment, the tip protector 601 comprises a locking mechanism 607 for temporarily limiting the distal opening size 606 within a predefined size opening value, which prevents the instrument tip 612 from passing through the distal through opening 605 of the tip housing 602 with the purpose of strengthening said constraining action.

According to a preferred embodiment, said tip protector 601 is made of two pieces 601' and 601", each of said two pieces 601' and 601" being a rigid body comprising at least one elastically flexible part.

As mentioned above, said surgical instrument 610 comprises a shaft 611 and an articulated instrument tip 612 at or near a distal portion 613 of the shaft 611, as diagrammatically shown in the example of FIG. 1*bis*. According to an embodiment, said articulated instrument tip is at the distal end of the shaft 611. Preferably, said instrument tip 612 of the surgical instrument 610 is articulated with respect to the shaft 611 of the surgical instrument 610 and is designed to operate within a predefined operatory volume 625. According to an embodiment, said shaft 611 of the surgical instrument 610 defines a longitudinal direction X-X, substantially coinciding with the axis of longitudinal development of the shaft 611. Preferably, said shaft 611 also defines a radial direction R-R orthogonal to the longitudinal direction X-X and incident the longitudinal direction X-X, and a circumferential direction C-C orthogonal to both the longitudinal direction X-X and the radial direction R-R. Preferably, the longitudinal, radial and/or and circumferential directions X-X, R-R, C-C are defined also on the tip protector 601 when considered alone. The longitudinal direction X-X coincides with the centerline x-x of the tip protector 601. The tip protector 601 may have a substantially symmetric body with respect to the centerline x-x, although according to some embodiments it does not have a symmetric body. The symmetry of the tip protector 612 may be functional with respect to said centerline x-x and/or to said longitudinal direction X-X of the shaft 611.

The shaft 611 may be a rigid straight shaft having a single axis of longitudinal development, or may be a rigid curved shaft, or may be a flexible shaft made of a chain of a plurality of shaft links having local axis of longitudinal development.

The surgical instrument 610 is preferably designed for performing robotic surgery, for example robotic-aided microsurgery and/or robotic-aided laparoscopic surgery, preferably as part of a master-slave robotic surgery system 620 comprising a master console 621 controlling the surgical instrument 610, as shown for example in FIG. 1.

As mentioned above, said tip protector 601 comprises a tip housing 602 or first housing 602 for releasably receiving the articulated instrument tip 612. The size, shape and material of the tip housing 602 may be chosen in order to receive the articulated instrument tip 612 of a specific surgical instrument 610.

According to an embodiment, said tip housing 602 comprises at least one protective distal wall 608 suitable for at least partially contouring the articulated instrument tip 612 in order to protect the tip from impact with other objects and/or anatomic parts as well as to protect the patient's anatomy from unwanted interaction with the articulated instrument tip 612 of the surgical instrument 610.

According to an embodiment, said tip housing 602 further comprises a proximal through opening 623. Thereby, the body of the tip housing 602 defines a proximal through opening 623, a distal through opening 605, and a housing cavity 624 therebetween.

According to an embodiment, said tip housing 602 comprises at least one tip abutment surface 609', 609", 609'", 609"" and preferably at least a pair of tip abutment surfaces 609', 609", 609'" 609'" suitable for abutting against the instrument tip 612 from opposite sides of the instrument tip 612 in a direction which is transverse to the longitudinal direction X-X of the shaft 611.

As mentioned above, said at least one tip abutment surface 609', 609", 609'", 609"" abuts against the articulated tip 612 from opposite sides of the articulated tip 612 in a direction which is transversal to the longitudinal direction X-X of the shaft 611. According to an embodiment, said at least one tip abutment surface 609', 609", 609'", 609"" may abut against the articulated tip 612 in the longitudinal direction X-X. Thereby, the instrument tip 612 abuts thereagainst in the longitudinal direction X-X and also in the radial direction R-R.

Preferably, said at least one tip abutment surface 609', 609", 609'", 609"" is able to prevent the articulated instrument tip 612 from being inclined in an unwanted inclination angle with respect to the shaft 611 when the tip protector 601 houses the tip 612.

According to an embodiment, said protective distal wall 608 of the tip housing 602 comprises said at least one abutment surfaces 609', 609", 609'", 609""; in other words, according to an embodiment, said at least one abutment surfaces 609', 609", 609'", 609"" belong to the protective distal wall 608.

According to an embodiment, the tip protector 601 comprises at least a pair of tip abutment surfaces 609', 609", 609'", 609"", preferably mutually opposite and facing said cavity of the housing 602, said pair of tip abutment surfaces 609', 609", 609'", 609"" comprises an abutment surface and an abutment countersurface suitable for abutting against the articulated instrument tip 612 from opposite sides thereof in the radial direction R-R, thereby preventing that the articulated instrument tip 612 could be inclined in an unwanted inclination angle with respect to the shaft 611 when the tip protector 601 houses the articulated tip 612. A pair of abutment surfaces comprising an abutment surface and an abutment countersurface may be formed by two portions of a same surface of the housing 602 of the tip protector 601. In the exemplary embodiment of the tip protector 601 shown in FIGS. 17 and 18, two pairs of tip abutment surfaces 609', and 609", 609'" and 609"" are shown, each pair comprising an abutment surface 609', 609'" and an abutment countersurface 609", 609"", and a pair of shaft abutment surfaces 629', 629" comprising a shaft abutment surfaces 629' shaft abutment countersurface 629" are also shown. Still referring to FIGS. 17 and 18, a pair of abutment surfaces 609', 609" abuts against a distal articulation of the articulated instrument tip 612 from opposite sides thereof, said distal articulation articulating the links 644, 645 and 646 about the yaw Y axis, thereby blocking the degrees of freedom of yaw and grip of the instrument tip 612.

Further, still referring to FIGS. 17 and 18, a pair of abutment surfaces 609'", 609"" abuts against an intermediate articulation of the instrument tip 612 from opposite sides thereof, said intermediate articulation articulating the links 643 and 644 about the pitch P axis, thereby blocking the degrees of freedom of pitch of the articulated instrument tip 612.

The articulated instrument tip 612 is preferably thinner than the shaft 611. In other words, the radial size of the articulated instrument tip 612 is preferably thinner than the radial size of the shaft 611.

Figure 15:
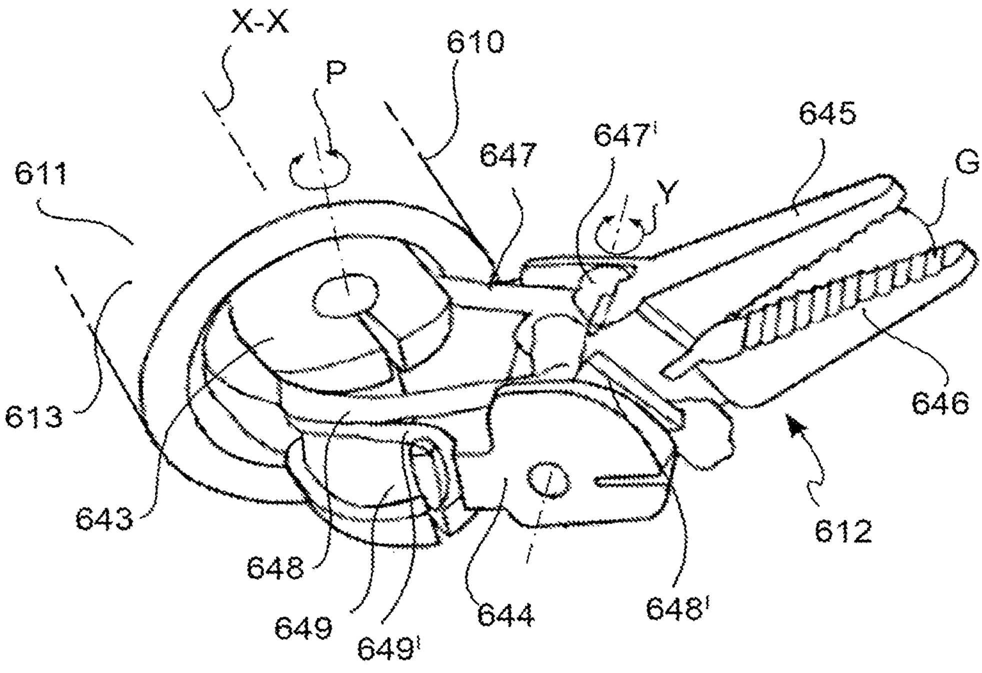
FIG. 15 is an axonometric view, which diagrammatically shows an instrument tip of a surgical instrument, according to an embodiment.

In the exemplary embodiment of the surgical instrument 610 shown in FIG. 15, the articulated tip 612 comprises pitch P, yaw Y and grip G degrees of freedom with respect to the shaft 611. Thanks to the provision of said abutment surfaces 609', 609", 609'", 609"" of the tip housing 602 designed to abut against the articulated instrument tip 612 it is made possible to position/orient the articulated instrument tip 612 in a predetermined configuration while the tip protector 601 is fit onto the instrument tip 612 and the tip housing 602 receives the instrument tip 612 abutting thereagainst. Thereby, thanks to said tip protector 601 equipped with such abutment surfaces 609', 609", 609'", 609"" within said tip housing 602, the degrees of freedom of the surgical instrument can be freezed in a predefined configuration. In other words, the tip protector 601 is able to temporarily constrain the degrees of freedom of the surgical instrument tip 612, for example at least some among pitch P, yaw Y and instrument grip G degree of freedom, and preferably at least the instrument grip G degree of freedom of the instrument tip 612. According to an embodiment, the tip protector 601 having said abutment surfaces 609', 609", 609'", 609"" constrains all the degrees of freedom of pitch P, yaw Y, and grip G of the instrument tip 612, when the tip protector 601 is fitted onto the instrument tip 612.

According to an embodiment, the tip protector 601 is also able to temporarily constrain the roll degree of freedom of the surgical instrument tip 612.

Preferably, the tip protector 601 temporarily constrains the articulated instrument tip 612 in a straight configuration, aligned along the longitudinal axis X-X of the instrument shaft 611. Thereby, when the tip housing 602 of the tip protector 601 is positioned or repositioned onto the instrument tip 612, the instrument tip 612 returns in said predefined straight configuration, as shown for example in FIG. 16.

The predefined configuration may be not straight, [i.e. a bent configuration] of the articulated instrument tip 612 forming for example a predefined bending angle with respect to the longitudinal direction X-X of the instrument shaft 611. Where there is more than one rotational degree of freedom, said bent configuration imposed by the tip protector 601 may define an array of predefined bending angles with respect to the longitudinal direction X-X of the instrument shaft 611.

The articulated instrument tip 612 may comprise a plurality of articulated links 643, 644, 645, 646 and driven by actuation cables or tendons 647, 647', 648, 648', 649, 649'. Preferably at least a portion of at least some of said tendons 647, 647', 648, 648', 649, 649' slides onto the external surfaces of some of the links 634, 644, 645, 646, said external surfaces preferably are ruled surfaces formed by straight lines all parallel one another and parallel to an axis of degree of freedom, e.g. pitch P and yaw Y of the articulated instrument tip 612. Articulated instrument tip 612 comprises, according to an embodiment, pitch P, yaw Y and instrument grip G degrees of freedom. According to an embodiment, the surfaces onto which the tendons 647, 647', 648, 648', 649, 649' slide are all made by wire electro-discharge machining, and preferably without requiring to individually reposition the links to be machined in a machining fixture. The machining fixture may be rotated to allow the machining of such surfaces. The articulated instrument tip 612 may comprise also a roll degree of freedom, in other words a rotational degree of freedom about the longitudinal direction X-X of the instrument shaft 611.

Preferably, the tip protector 601 constrains in a predefined configuration the instrument tip 612 when the tip 612 is received into said tip housing 602 and said one or more abutment surfaces 609', 609", 609'", 609"" of the tip protector 601 abut against one or more portions [i.e. links 643, 644, 645, 646] of said articulated instrument tip 612. To this end further one or more shaft abutment surfaces 629', 629"

may be provided on the tip protector 601 to abut against the instrument shaft 611 of the surgical instrument 610.

As mentioned above, said tip protector 601 preferably comprises a clamp system 603, suitable for gripping/clamping a portion of the surgical instrument 610. According to a preferred embodiment, said clamp system 603 is designed to grip/clamp a portion of the shaft 611 of the surgical instrument 610 to firmly position the repositionable tip protector 601. Thereby, a grip/clamp action against the shaft 611 of the surgical instrument 610 is exerted by said clamp system 603.

According to an embodiment, said claim system 603 comprises said further one or more shaft abutment surfaces 629', 629" of the tip protector 601. In other words, according to an embodiment, said one or more shaft abutment surfaces 629', 629" belong to the clamp system 603 of the tip protector 601. According to an embodiment, said one or more shaft abutment surfaces 629', 629" belong to the housing 602 of the tip protector 601.

According to an embodiment, said clamp system 603 comprises at least one elastic portion, such as a clip and/or an elastic tongue 615, biased towards the gripping of a portion of the surgical instrument 610. Thereby, the grip action is an elastic grip action exerted by means of elastic return of an elastic element such as a clip and/or an elastic tongue 615. Preferably, such an elastic grip action is directed substantially along the radial direction R-R. According to an embodiment, said elastic tongue 615 of the clamp system 603 comprises a base root and a free end, and at least one clamping abutment portion 616 at or near the free end of the elastic tongue 615. The clamping abutment portion 616 may be an enlarged head of the elastic tongue 615. A projection designed for projecting radially inwards, i.e. towards the shaft 611, may be provided at the free end of the tongue 615 and may form the clamping abutment portion 616.

According to a preferred embodiment, said clamp system 603 is designed to substantially surround the shaft 611. To this end, the clamp system 603 comprises a sleeve 617 that may be made of two half pipes 617' and 617", the sleeve 617 of the clamp system 603 is a through sleeve 617 forming a through channel 618 along the longitudinal direction X-X. Said through channel 618 thereby has a first proximal channel mouth 622 and a second opposite distal channel mouth 622' and the through channel 618 extending therebetween. Said clamping abutment portion 616 may preferably be part of the sleeve 617 defining said through channel 618. Said sleeve 617 may be preferably rigid so that not to conform to bends of the shaft, if any 611. Thereby, the proximal channel mouth 622 and the distal channel mouth 622' results substantially aligned.

According to a preferred embodiment, said half pipes 617' and 617" each comprises at least one elastic tongue 615 having a free end and said at least one clamping abutment portion 616 projecting radially inwardly from said free end.

According to an embodiment, said clamp system 603 comprises a latch mechanism for gripping a portion of the surgical instrument 610. Thereby, the grip action against a portion of the surgical instrument 610 is exerted by means of tightening of the latch mechanism.

According to an embodiment, said clamp system 603 comprises a threaded coupling for gripping a portion of the surgical instrument 610. Thereby, the grip action against a portion of the surgical instrument 610 is exerted by means of tightening the threaded coupling.

According to an embodiment, said at least one clamping abutment portion 616 of the clamp system 603 comprises a clamping abutment surface 619 that is designed to elastically bias in the radial direction R-R against the shaft 611 of the surgical instrument 610 with the purpose of positioning the tip protector 601 against the shaft 611. Thereby, thanks to such an elastic bias in the radial direction R-R, said clamping abutment surface 619 is in frictional contact with the shaft 611.

Thanks to said frictional contact, it is possible to prevent unwanted sliding of the tip protector 601 and particularly of the clamp system 603 thereof on the shaft 611.

According to an embodiment, said at least one clamping abutment portion 616 of the clamp system 603 corresponds to said one or more further shaft abutment surfaces 629', 629".

As mentioned above, said tip protector 601 preferably comprises a distal through opening 605, preferably located at or near the distal end 690 of the tip housing 602. According to an embodiment, said at least one protective distal wall 608 of the tip housing 602 delimits said distal through opening 605 of the tip protector 601. Said distal through opening 605 of the tip housing may serve for drainage of liquids from the housing cavity 624 of the tip housing 602 of the tip protector 601.

As mentioned above, said distal through opening 605 has an opening size 606 that is adjustable. Thereby, said distal through opening 605 can be made through for at least the instrument tip 612, to pass through said distal through opening 605 of the tip housing 602 of the tip protector 601. In other words, the size 606 of the distal through opening 605 of the tip housing 602 is adjustable and can be adjusted with the purpose of making the distal through opening 605 a through passage for at least the tip 612 of the surgical instrument 610. Preferably, said distal through opening 605 is a through opening also a portion of the shaft 611 of the surgical instrument 610. The tip protector can thereby be positioned and repositioned at various locations along the shaft 611 of the surgical instrument. According to a preferred embodiment, the term "opening size 606" as used herein refers to the dimensions of the distal through opening 605 that are evaluated in a direction transverse to the longitudinal direction X-X, and preferably along the radial direction R-R. According to a preferred embodiment, the term "opening size 606" as used herein refers to the diameter of the distal through opening 605. Thanks to such a distal through opening 605, the tip housing 602 of the tip protector may become a through channel for the instrument tip 612 and preferably also for at least a distal portion 613 of the shaft 611, and more preferably for the shaft 611 in its entirety. Thanks to the size adjustment of such a distal through opening 605 of the tip housing 602, the tip housing 602 may form a longitudinal abutment for the instrument tip 612 and by means of adjustment of the size 606 of the distal through opening 605 the tip housing 602 becomes a through longitudinal passage for the instrument tip 612.

According to a preferred embodiment, the size 606 of the distal through opening 605 is adjustable and can be set in an abutment configuration wherein said tip abutment surfaces 609', 609", 609'", 609"" abut against said instrument tip 612, and in a pass-through configuration wherein at least said instrument tip 612 passes through said distal through opening 605. When in the pass-through configuration the tip abutment surfaces 609', 609", 609'", 609"" of the tip housing 602 may abut against the shaft 611 of the surgical instrument 610.

According to an embodiment, the opening size 606 of the distal through opening 605 can be adjusted so that to temporarily close said distal through opening 605. The distal through opening 605 can be then adjusted in size to open. According to an embodiment, the opening size 606 of the distal through opening 605 can be adjusted so that to temporarily close said distal through opening 605, this configuration may correspond to an abutment configuration where said tip abutment surfaces 609', 609", 609'", 609"" abut against said instrument tip 612.

Figure 2:
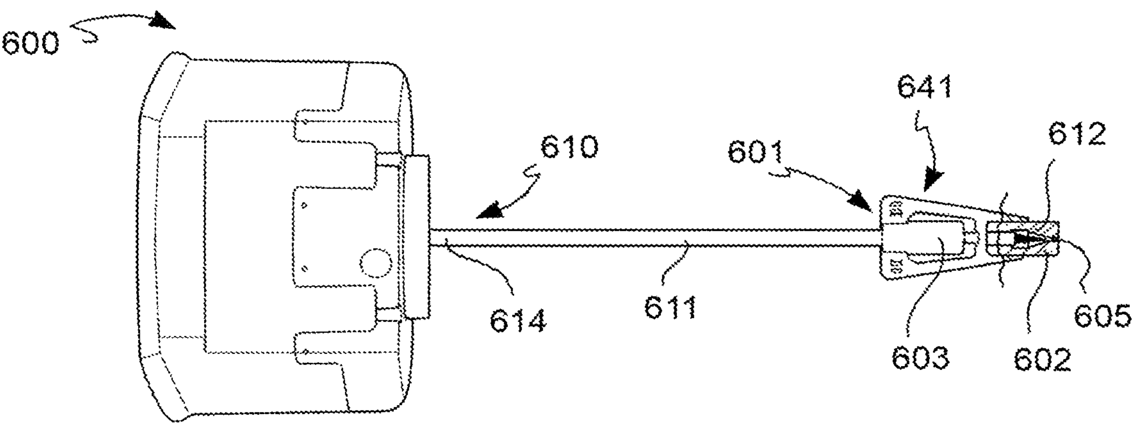
Figure 3:
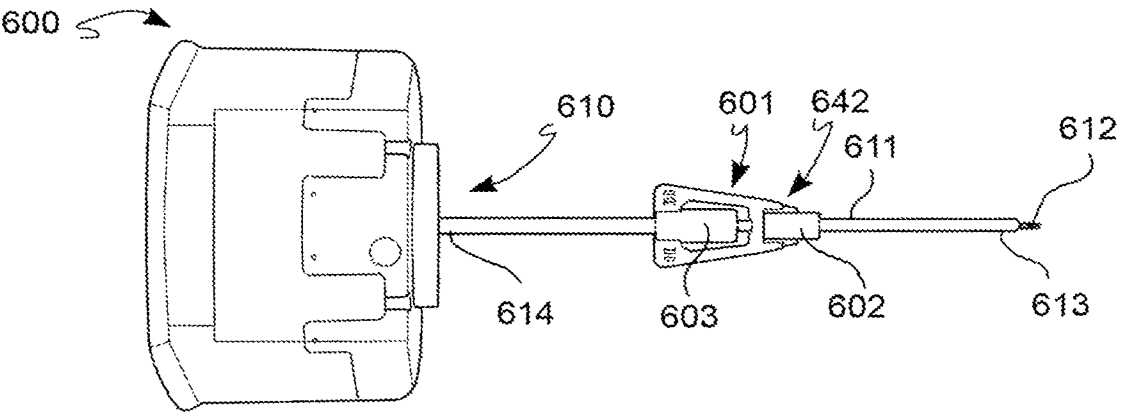
Figure 4:
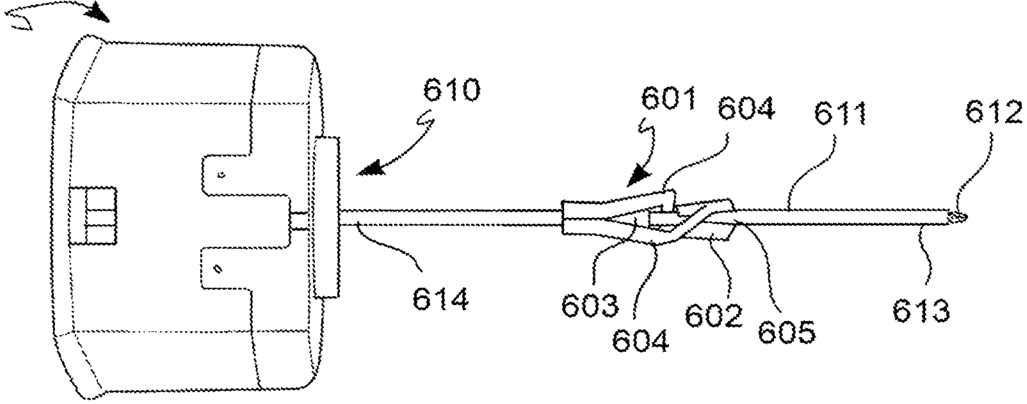
Figure 5:
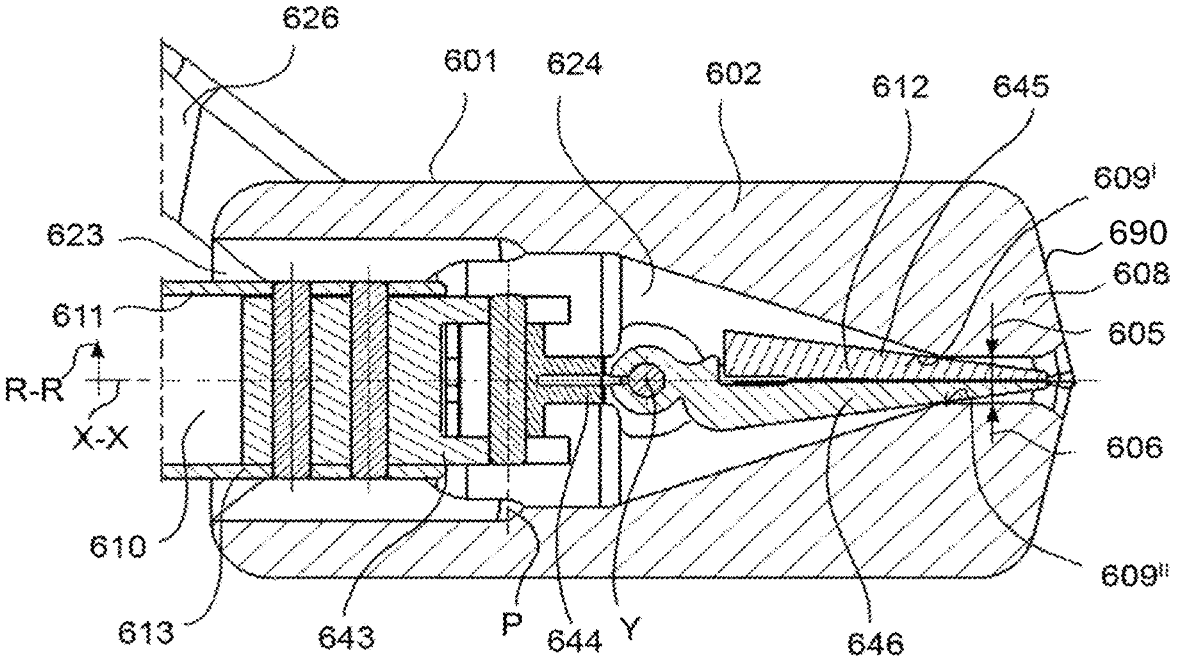
FIG. 5 is a cross-section along the longitudinal direction showing a tip protector covering an instrument tip, according to an embodiment.
Figure 6:
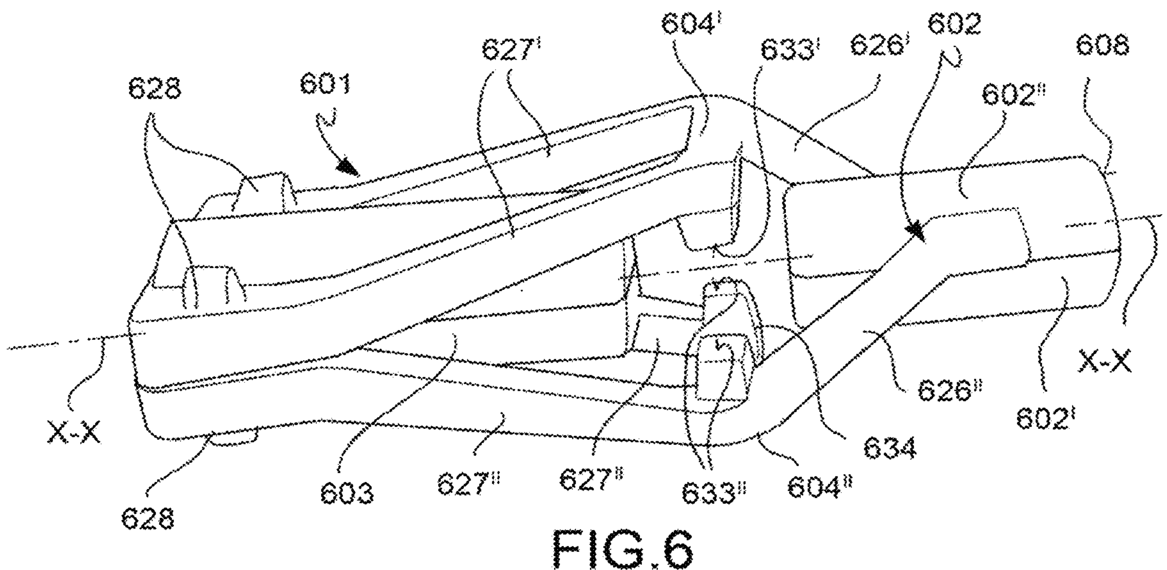
FIG. 6 is an axonometric view showing a tip protector, according to an embodiment.
Figures 7, 8:
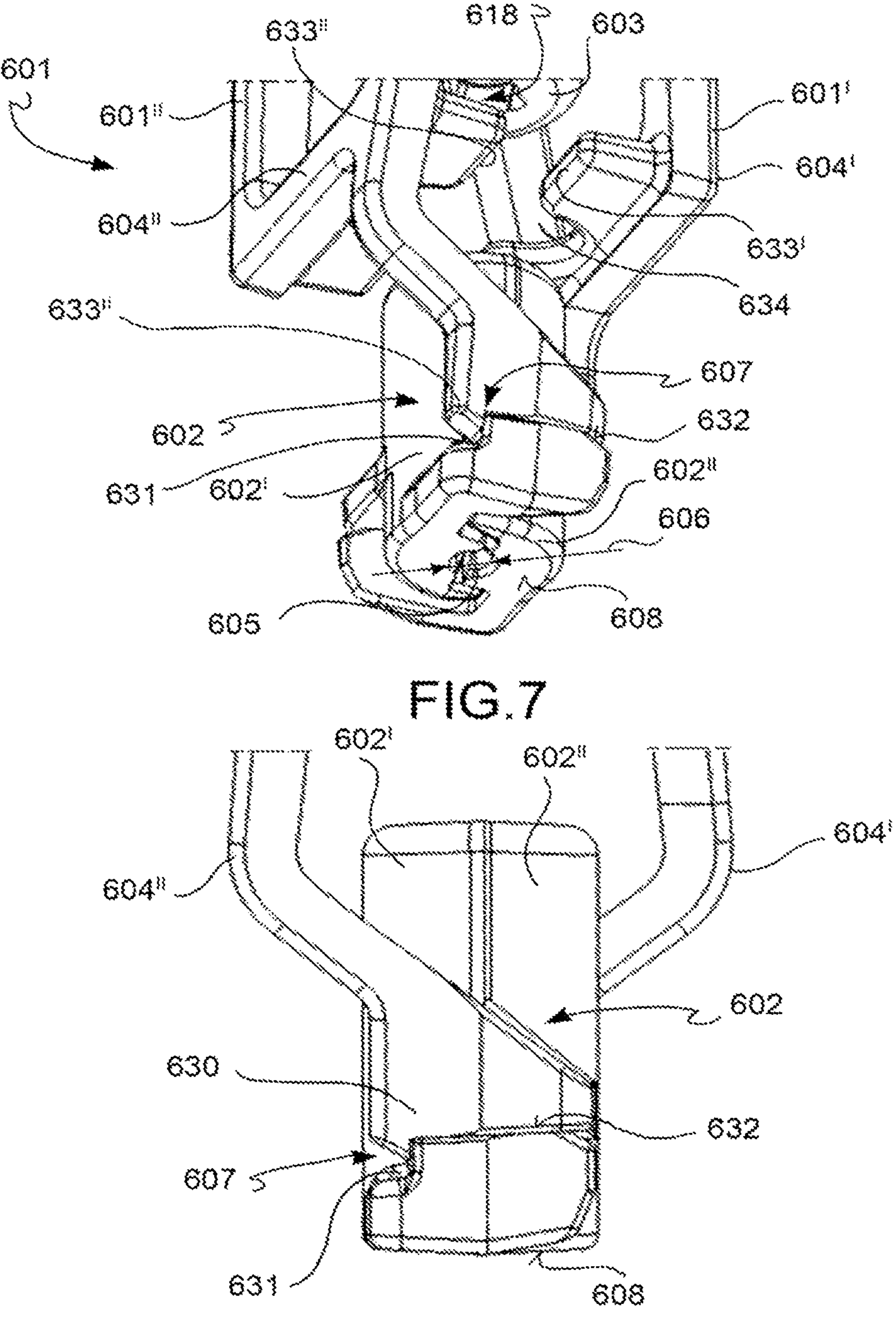
FIG. 7 is an axonometric view showing a tip housing of a tip protector, according to an embodiment.
FIG. 8 is an elevation side view according to the point of view indicate by the arrow VIII of FIG. 7.
Figure 9:
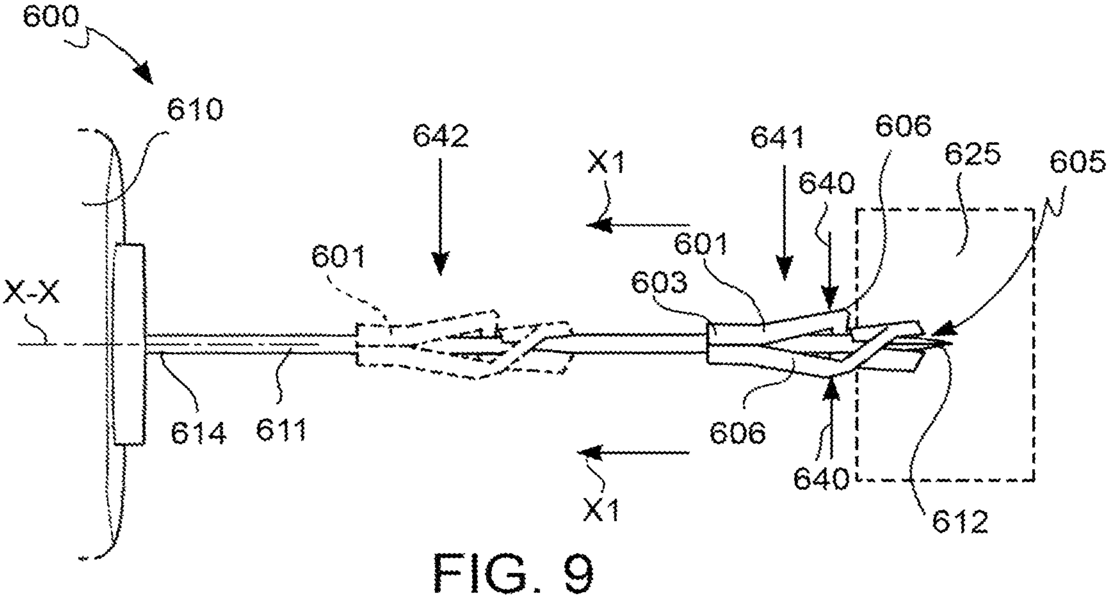
FIGS. 9 and 10 are elevation side views showing diagrammatically a tip protector clamped against different portions of the shaft of a surgical instrument, according to an embodiment, as well as some steps of a method according to a possible mode of operation.

When in operative conditions, the tip protector 601 is positioned in a certain location so that the instrument tip 612 of the surgical instrument 610 approaches the proximal mouth 622 of the though channel 618 defined by said clamp system 603. Then, the tip protector 601 is retracted along the longitudinal direction X-X along the shaft 611 of the surgical instrument 610 towards the proximal portion 614 of the shaft 611, as indicated by the retraction arrows X1 of FIG. 9. Thereby, the clamp system 603, preferably the sleeve 617 and the elastic tongue 615, of the tip protector 601 slidingly fits the distal portion 613 of the shaft 611 of the surgical instrument 610 and the articulated instrument tip 612 approaches the proximal through opening 623 of the housing cavity 624 of the tip housing 602 of the tip protector 601. Then, the tip protector 601 is further retracted along the longitudinal direction X-X along the shaft 611 of the surgical instrument 610 towards the proximal portion 614 of the shaft 611, as indicated by the retraction arrows X1 of FIG. 9.

Thereby, the at least one abutment portion 616 of the clamping system 603 abuts against the shaft 611 of the surgical instrument 610 exerting the elastic grip action against the shaft 611 to firmly position the tip protector 601 against the shaft 611. At this point, the size 606 of said distal through opening 605 of the tip housing 602 may be adjusted, in particular it may be increased. Thereby, the distal through opening 605 becomes a pass-through opening of the instrument tip 612 as the size 606 of the distal through opening 605 when in the pass-through configuration exceeds the radial size of the instrument tip 612. Then, the tip protector 601 is further retracted along the longitudinal direction X-X along the shaft 611 of the surgical instrument 610 towards the proximal portion 614 of the shaft 611, as indicated by the retraction arrows X1 of FIG. 9.

The tip protector 601 can thereby be repositioned, i.e. against the shaft 611, at a new location that is for example located proximal along the shaft 611 to the previous location, thereby exposing the instrument tip 612 distally with respect to the tip housing 602, in other words: the articulated instrument tip 612 protrudes in the longitudinal direction X-X distally from the protective distal wall 608 of the tip housing 602.

Thanks to such a tip protector 601 it is possible to expose the instrument tip 612 that was previously covered by the same tip protector 601 and in particular by the tip housing 602, without requiring to move the surgical instrument 610 away from the operatory volume 625 and therefore without requiring to reposition the surgical instrument 610 and the instrument tip 612 thereof within the operatory volume 625. Thanks to such a tip protector 601 the exposure of the instrument tip 612 is achieved by means of retraction of the tip protector 601 relatively to the instrument shaft 611.

At the same time, by means of retracting the tip protector 601 having the adjustable distal through opening 605 towards the proximal end 614 of the shaft 611 while the tip protector 601 is still fitted onto the shaft 611, it is allowed to reduce the volume of free space around the surgical instrument 610 that is needed in order to expose the instrument tip 612. In particular, as the tip protector 601 is repositionable in a retracted position against and along the shaft 611, in order to expose the instrument tip 612 it suffices to retract the tip protector 601 accordingly, thereby avoiding the need of extracting the tip protector from the distal end of the shaft. Thereby, the tip protector 601 makes the exposure of the instrument tip 612 quicker and safer when compared to known solutions. Moreover, the safety of the surgery is further enhanced as it is made possible to position the instrument tip 612 at the desired location before the removal of the tip protector 601 from the instrument tip 612.

Figure 10:
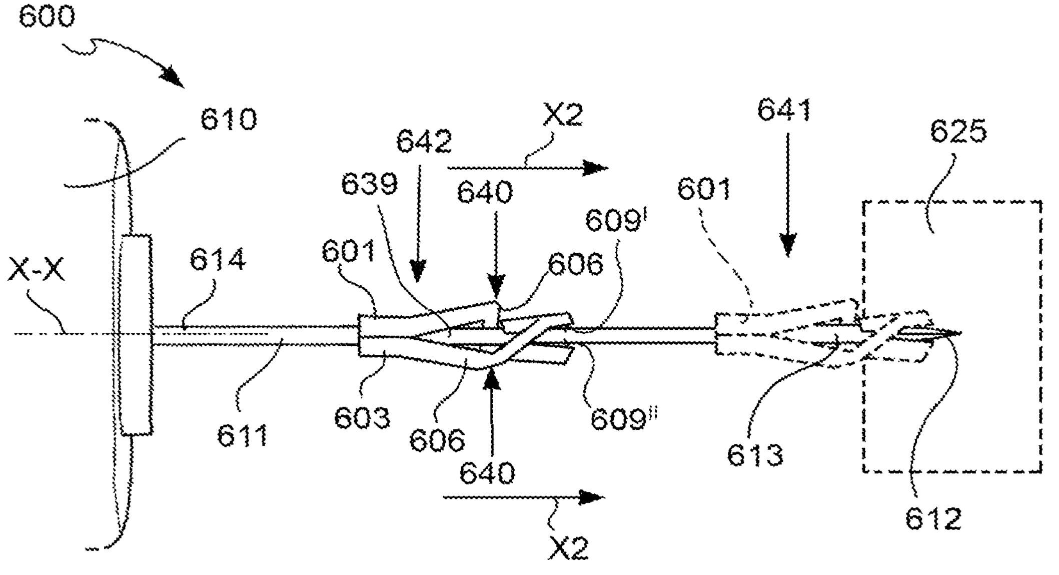
Figure 11:
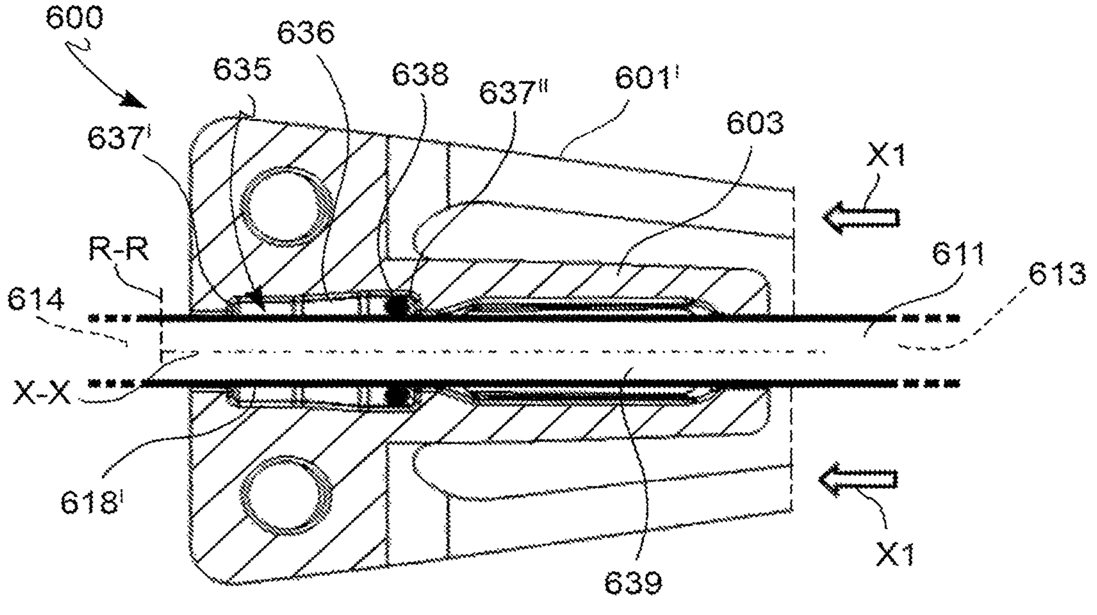
FIGS. 11 and 12 are cross-sectional views of a tip protector, according to an embodiment, fitted onto the shaft of a surgical instrument, as well as some steps of a method according to a possible mode of operation.
Figure 12:
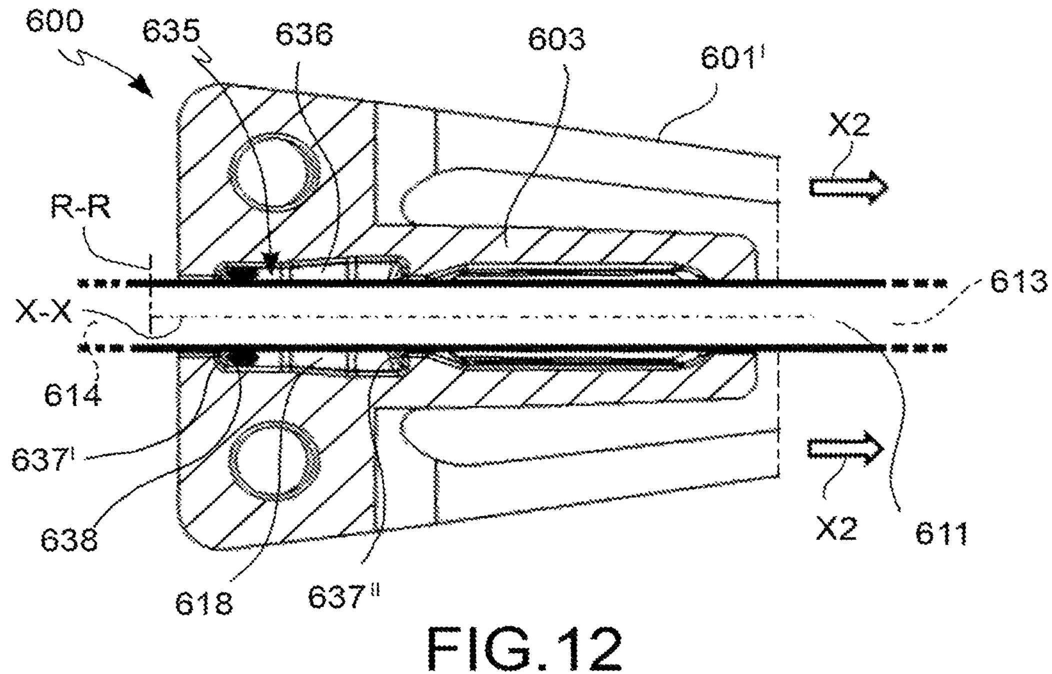
Figure 13:
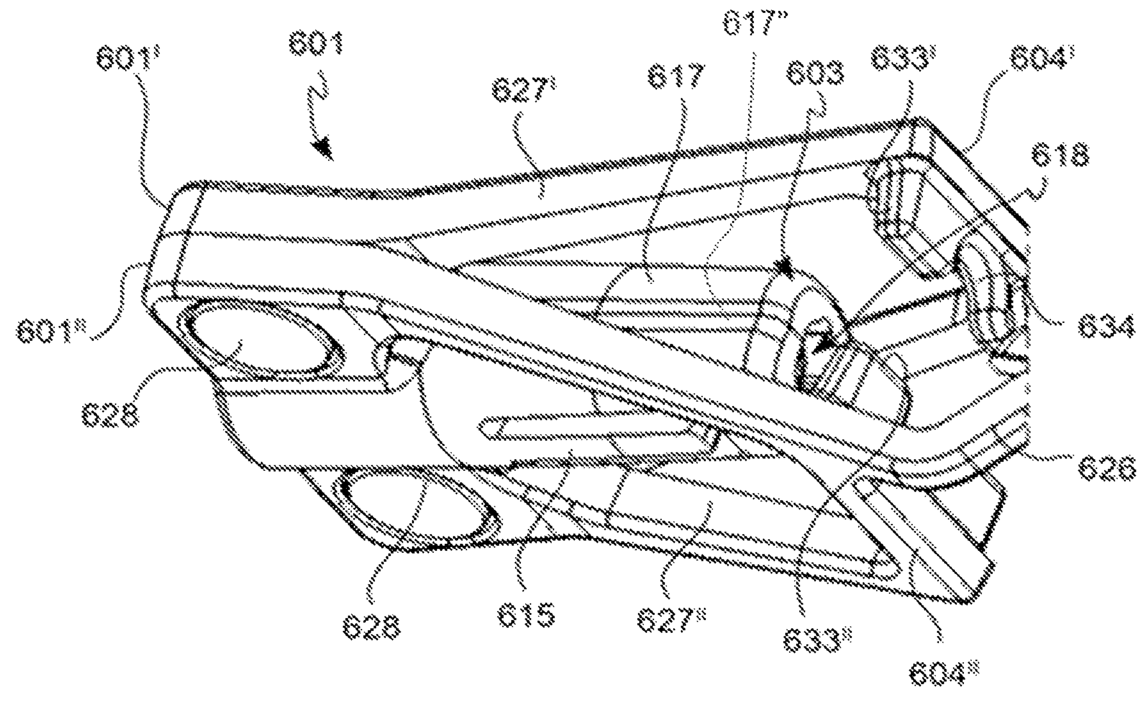
FIG. 13 is an axonometric view showing the clamping system of a tip protector, according to an embodiment.
Figure 14:
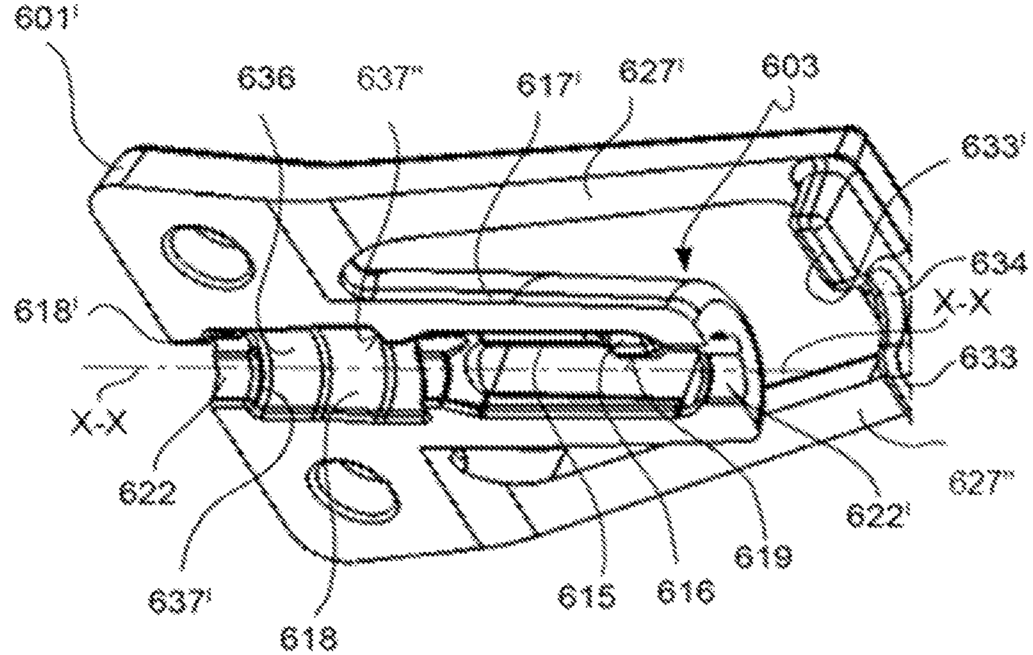
FIG. 14 is an axonometric view of the tip protector of FIG. 13 wherein only one of two pieces of the tip protector is shown.

Moreover, it is made possible to cover or to protect the instrument tip 612 by means of said tip protector 601 before moving the surgical instrument 610 away from the operatory volume 625. The covering of the instrument tip 612 is achieved by advancing the tip protector 601 along the shaft 611 away from the proximal end 614 of the shaft 611, towards and beyond the distal portion 613 of the shaft 611, as indicated by the arrow X2 of FIG. 10. In this configuration, clamping system 603 abuts against the shaft 611 at a location which is near to the instrument tip 612. Moreover, when the tip protector 601 covers the articulated instrument tip 612, the at least one abutment surface 609', 609", 609'", 609"" of the housing 602 abuts against the articulated instrument tip 612 from opposite sides thereof, exerting a constraining action, which brings the links forming the articulated instrument tip 612 in a predefined configuration. The predefined configuration may be aligned to the shaft 611.

The provision of such one or more shaft abutment surfaces 629', 629" abutting against the shaft 611 at a location near to the instrument tip 612 allows for strengthening the constraining action exerted by the at least one abutment surface 609', 609", 609'", 609"" of the tip protector 601.

According to an embodiment, the tip protector 601 transmits any loads to the shaft 611 avoiding to overloading the instrument tip 612. For example, any loads applied onto the distal wall 608 of the tip protector 601 is transmitted to the instrument shaft 611. Thereby, the safety of the surgery for the patient and the integrity of the instrument tip 612 are greatly enhanced.

According to an embodiment, the tip protector 601 is made of a molded rigid plastic material, for example through injection molding. Thereby the tip protector 601 can be disposable [i.e. single use] and at the same time unexpensive to manufacture.

According to an embodiment, the tip protector 601 is made of a material that can be sterilized, for example with conventional sterilization procedures for surgery.

According to an embodiment, said tip protector 601 comprises a control interface 604 for controlling the adjustment of the opening size 606 of said distal through opening 605. By acting onto said control interface 604, it is possible to adjust the size 606 of the distal through opening 605. According to an embodiment, said control interface 604 is connected to at least one transmission element 626 that is in turn connected to at least one portion of the tip housing 602, so that the at least one transmission element 626 transmits a control action from the control interface 604 to the tip housing 602 with the purpose of adjusting the distal through opening 605 of the tip protector 601. According to an embodiment, said control interface 604 comprises at least one interface surface 604', 604", and preferably two opposite interface surfaces 604', 604" located opposite one another with respect to the tip housing 602, and the at least one transmission element 626 comprises a first transmission arm 626' and a second transmission arm 626", wherein each interface surface 604' or 604" is integrally connected to a respective of said transmission arms 626' or 626". According to an embodiment, said control interface 604 comprises at least two opposite interface surfaces 604', 604" located opposite one another with respect to the tip housing 602, wherein at least one of the at least two interface surfaces 604', 604" is associated to an elastic element 627, for example an elastic arm 627' or 627" integrally connected to a respective interface surface 604', 604", so that the elastic element 627 biases said at least one of the at least two interface surfaces 604', 604" towards a predefined position. Preferably, said predefined position towards which the at least one elastic element 627 biases the at least one interface surface 604', 604" determines the tip housing 602 to assume said abutment configuration. According to an embodiment, said two opposite interface surfaces 604', 604" are designed to be pressed towards one another by the fingers of an operator.

The pressure manually applied onto said two opposite interface surfaces 604', 604" determines the elastic deformation, i.e. bending, of the at least one elastic element 627 and at the same time displaces a portion of the tip housing 602 by means of said at least one respective transmission element 626. Preferably, said tip housing 602 is formed by at least two parts 602' and 602" or tip half-housings 602' and 602" that cooperate together to define said tip hosing 602, and wherein each of said two opposite interface surfaces 604', 604" is associated to a respective tip half-housing 602', 602" through a respective transmission element 626', 626". The paths described by said transmission elements 626' and 626" may overlap along the centerline x-x of the tip protector 601, so that applying a pressure onto said first interface surface 604' determines the displacement of the first tip half housing 602' that is located on the opposite longitudinal side of the tip protector 601 with respect to the first interface surface 604'.

According to an embodiment, said tip protector 601 is substantially a clip having the size 606 of the distal opening 605 elastically adjustable and the abutment surfaces 609', 609", 609'", 609"" elastically preloaded in closure [i.e. toward each other].

Said at least two elastic arms 627', 627" for biasing the respective interface surface 604', 604" and/or abutment surfaces 609', 609", 609'", 609"" may be integrally fixed one to the other in a respective fixing root 628 thereof so that the respective interface surfaces 604' and 604" substantially protrude in the radial direction R-R preferably forming a bend on the body of the respective elastic arm 627', 627", from each of the surface interfaces 604', 604" extends a respective transmission arm 626', 626" that extends towards the centerline x-x of the tip protector 601 and that connects to a respective tip half-housing 602', 602" located on the opposite longitudinal side with respect to the respective interface surface 604' or 604".

According to an embodiment, said tip protector 601 is made of two pieces 601' and 601" locally integrally fixed to one another in said fixing root 628 so that the elastic arms 627' and 627" elastically bias the respective interface surfaces 604' and 604" to protrude radially away from the centerline x-x, and wherein each interface surface 604', 604" is connected to a respective tip half-housing 602', 602" by means of a respective transmission arm 626', 626", and wherein the tip half-housings 602', 602" together define preferably partially said distal through opening 605, and at the same time the elastic arms 627' and 627" elastically bias the respective abutment surfaces 609', 609", 609'", 609"" towards each other.

Fixing means may be provided to fix said two pieces 601' and 601" of said tip protector 601, for example said fixing means comprises: at least one rivet, and/or at least one screw, and/or at least one nail, and/or glue and/or the like.

According to an embodiment, said tip protector 601 comprises one or more stroke end portions 633 for limiting the maximum size 606 of the distal opening aperture 605. Thereby, it prevents abutment to overstress the elastic elements of the tip protector 601. According to an embodiment, said one or more stroke end portion 633 are at least two facing stroke end portions 633' and 633" preferably each of said at least two facing stroke end portions 633' and 633" is located opposite to a respective interface surface 604' 604" of the tip protector 601. According to an embodiment, each of said at least two facing stroke end portions 633' and 633" is located on the same piece of material of a respective interface surface 604' 604" and behind it. According to an embodiment, said one or more stroke end portions 633' and 633" are in the form of protrusions extending towards the tip protector centerline x-x. According to an embodiment, a through longitudinal passage 634 is defined in said stroke end portions 633' and 633" to receive the shaft 611 of the surgical instrument 610.

According to an embodiment, said tip protector 601 comprises a locking mechanism 607 for temporarily limiting the distal opening size 606 within a predefined size opening value that prevents the instrument tip 612 from passing through the distal through opening 605 of the tip housing 602. Thanks to the locking mechanism 607 it is possible to temporarily block the maximum size of the distal through opening 605 when the tip protector 601 has the at least one abutment surface 609', 609", 609'", 609"" in abutment against the articulated instrument tip 612 and/or the shaft abutment surfaces 629, 629' in abutment against the shaft 611 with the purpose of exerting said constraining action. At the same time, that allows for a more firm positioning of the tip protector 601 against the shaft 611. Thereby the size 606 of the distal through opening 605 is independent from the clamping action of the clamping system 603, and that may allow an improved clamping force.

Moreover, thanks to the provision of said locking mechanism 607, the occurrence of an unwanted motion of the instrument tip 612 in the radial direction R-R avoids adjusting the size 606 of the distal through opening 605. Preferably, said locking mechanism 607 comprises at least one locking tooth 630 located on a tip half-housing 602' or 602" near the distal through opening 605 that engages with a respective locking notch 631 of the other tip half-housing 602" or 602'. Preferably, each half housing has one locking tooth. Preferably, said locking mechanism 607 comprises further a cam surface 632 to favor the engagement and/or the disengagement of said at least one locking tooth 630 with a respective locking notch 631 though roll of a portion of one of the tip half housing 602' or 602" over said cam surface 632 that is located on the other tip half-housing 602" or 602'. Thereby the cam surface 632 while rolling defines a fulcrum for engaging and/or disengaging said tip half-housings 602' and 602". According to an embodiment, the locking tooth 630 during the process of closure of the distal opening is elastically biased against said cam surface 632. According to a preferred embodiment, when the locking mechanism 607 is activated, it resists against the elastic bias exerted by arms of the tip protector 601, so that when locked the tip protector 601 is elastically deformed.

According to an embodiment, said clamping system 603 of the tip protector 601 comprises an anti-twist device 635 designed to avoid or at least to reduce the roll or twist or pivot of the instrument shaft 611 with respect to the tip protector 601 about the longitudinal direction X-X while the tip protector 601 is clamped to the instrument shaft 611.

According to an embodiment, said anti-twist device 635 comprises at least one o-ring 638 fitted onto the shaft 611 and received with clearance in a chamber 636 of the through channel 618 of the clamping system 603; said chamber 636 has walls defining at least a proximal o-ring stroke end 637' and a distal o-ring stroke end 637", each acting as stroke end wall for the o-ring 638, wherein near or at one of the o-ring stroke ends 637' or 637" the walls of the chamber 636 define a narrower through passage 618' that pinch the o-ring 638 thereby preventing through the body of the o-ring 638 the relative roll or twist or pivot of the shaft 611 within said through passage 618 of the clamping system 603. Preferably, said proximal o-ring stroke end 637' defines the narrower through passage 618'. The term "narrower through passage" does not necessarily means that is the narrowest section of the through channel 618, although it can be according to some embodiments.

According to an embodiment, said anti-twist device 635 comprises one or more guiding elements, such as one or more guiding grooves or guiding protrusions. designed to guide the tip protector 601 along the shaft 611 along a predetermined direction. The shaft 611 may suitably comprise one or more counter-guiding elements, such as guiding protrusions or guiding grooves designed to engage with the one or more guiding elements of the tip protector 601. The predetermined direction may be a straight direction parallel to longitudinal extension of the shaft X-X. The predetermined direction may be a helicoidal direction winding around the shaft 611 and extending along longitudinal extension of the shaft X-X. The provision of such one or more counter-guiding elements of the shaft 611, designed to engage with the one or more guiding elements of the tip protector 601 allows an enhanced control over the relative displacement of the tip protector 601 and the shaft 611, allowing to define at least one repositioning path for the tip protector 601 with respect to the shaft 611 and/or the instrument tip 612, thereby preventing the tip protector 601 to rotate about the longitudinal direction X-X without control during repositioning of the tip protector 601 along the shaft 611 and/or against the instrument tip 612. In this way, when the tip protector 601 is moved distally from the shaft 611 to abut against the instrument tip 612, it is possible to ensure that the tip protector 601 abuts against a predetermined portion of the instrument tip 612.

According to an embodiment, at least one tip abutment surface 609', 609", 609'", 609"" of a pair of opposite tip abutment surfaces is made as a single piece with at least one shaft abutment surface 629', 629" of a pair of opposite shaft abutment surfaces. Elastic elements may be also provided between said at least one tip abutment surface 609', 609", 609'", 609"" of a pair and said at least one shaft abutment surface 629', 629" of a pair. The provision of the locking mechanism may lock the relative position of said at least one tip abutment surface 609', 609", 609'", 609"" of a pair and at least one shaft abutment surface 629', 629" of a pair, acting against the elastic preload provided by said elastic element thereby constraining a respective half of the tip protector 601 in an elastically deformed configuration.

According to an embodiment, at least one tip abutment surface 609', 609", 609'", 609"" of a pair of opposite tip abutment surfaces is made as a single piece with at least one clamping abutment portion 616 of a pair of opposite clamping abutment portions of the clamping system of the tip protector 601. Thereby, a pair of opposite clamping abutment portions may be provided. Elastic elements may be also provided between said at least one tip abutment surface 609', 609", 609'", 609"" of a pair and said at least one clamping abutment portion 616 of a pair. The provision of the locking mechanism may lock the relative position of said at least one tip abutment surface 609', 609", 609'", 609"" of a pair and said at least one clamping abutment portion 616 of a pair, acting against the elastic preload provided by said elastic element thereby constraining a respective half of the tip protector 601 in an elastically deformed configuration.

According to a general embodiment, an assembly 600 comprises at least one tip protector 601 according to any one of the embodiments described above.

Said assembly 600 also comprises at least one surgical instrument 610 having a shaft 611 according to any one of the embodiments described above. Preferably, said assembly 600 comprises a surgical instrument 610 having a shaft 611 extending along a longitudinal direction X-X and an articulated instrument tip 612 at the distal portion 613 of the shaft 611.

Said articulated instrument tip 612 is articulated with respect to the instrument shaft 611 defining at least one degree of freedom.

The tip protector 601 is fitted onto the shaft 611 of the surgical instrument 610, so that the tip protector 601 is repositionable in various locations along the shaft 611.

The tip housing 602 comprises at least one tip abutment surface 609', 609", 609'", 609"" suitable for abutting against the instrument tip 612 from opposite sides thereof for exerting a constraining action on the instrument tip 612 at least in a direction, which is transversal to the longitudinal direction X-X of the shaft 611, with the purpose to block at least one of the degrees of freedom of said articulated instrument tip 612.

According to a preferred embodiment, the articulated instrument tip 612 has at least one degree of freedom of grip G, wherein said constraining action exerted by said at least one abutment surface 609', 609", 609'", 609"" constrains the degree of freedom of grip G in a predefined configuration.

According to a preferred embodiment, the articulated instrument tip 612 has at least one between pitch P and yaw Y degree of freedom, and preferably both, wherein said constraining action exerted by said at least one abutment surface 609', 609", 609'", 609"" constrains at least one the degree of freedom of pitch P and/or yaw Y in a predefined configuration.

According to a preferred embodiment, said predefined configuration is a straight configuration aligned to the longitudinal direction X-X of the instrument shaft 611, so that said constraining action exerted by said at least one abutment surface 609', 609", 609'", 609"" constrains the articulated instrument tip 612 in a straight configuration aligned to the longitudinal direction X-X of the instrument shaft 611.

According to a preferred embodiment, said instrument tip 612 of the surgical instrument 610 comprises one or more tendons 647, 647', 648, 648', 649, 649' for articulating said one or more degree of freedom of the articulated instrument tip 612, wherein said constraining action exerted by the at least one abutment surface 609', 609", 609'", 609"" blocks at least one of the degrees of freedom of said articulated instrument tip 612 even when said one or more tendons 647, 647', 648, 648', 649, 649' apply a tensile load directed to actuate at least one of the degrees of freedom of said articulated instrument tip 612. That is achievable for example thanks to the provision of at least one suitably tuned elastic element of the tip protector 601, which makes the constraining action an elastic constraining action, and/or thanks to the provision of a locking mechanism of the tip protector 601.

As mentioned above, the at least one tip protector 601 is repositionably fitted onto the shaft 611 of the at least one surgical instrument 610.

According to an embodiment, said shaft 611 of the surgical instrument 610 comprises a counter-clamping portion 639 suitable for the clamping system 603, preferably said abutment portion 616 of the clamping system 603, to abut thereon and/or there against in order to avoid the tip protector 601 to slip out from the shaft 611.

According to an embodiment, said counter clamping portion 639 of the shaft 611 of the surgical instrument 610 has a surface treatment for enhancing the longitudinal friction and thus the adhesion with the clamping system 603. Preferably, said surface treatment is made by knurling.

According to an embodiment, said counter clamping portion 639 of the shaft 611 has a protuberance for engaging with, for example in an undercut manner, the clamping system 603 of the tip protector 601. The counter clamping portion of the shaft may engage with the clamping portion of the tip protector according to any suitable strategies, for example by means of form-fitting, and/or threaded coupling, and/or force-fitting, and/or the like.

According to a general embodiment, a master-slave robotic surgery system 620 comprises at least one assembly 600 according to any one of the embodiments described above and a master console 621 for controlling the surgical instrument 610 of said assembly 600.

In the following will be described a method of repositioning of a tip protector 301.

A method for repositioning a tip protector 601 comprises the steps of:

- positioning a tip protector 601 against a first portion 641 of the shaft 611 of a surgical instrument 610 that has an instrument tip 612 near the distal portion 613 of the shaft 611;
- applying an action 640 onto an interface 604 of the tip protector 601 so that to increase the size 606 of a distal through opening 605 of said tip protector 601, thereby the distal through opening 605 becomes a through passage for at least the instrument tip 612;
- moving the tip protector 601 along the shaft 611;
- repositioning the tip protector 601 against a second portion 642 of the shaft 611.

According to a preferred mode of operation, the step of repositioning involves the step of releasing the action 640. Preferably, said action 640 is a manual action 640.

According to a mode of operation, the second portion 642 of the shaft 611 is closer to a proximal end 614 of the shaft 611 than the first portion 641 of the shaft 611 along the longitudinal direction X-X.

According to a mode of operation, the second portion 642 of the shaft 611 is farther to a proximal end 614 of the shaft 611 than the first portion 641 of the shaft 611 along the longitudinal direction X-X.

According to a mode of operation, the method comprises the step of further repositioning the tip protector 601 against the shaft 611 of the surgical instrument 610.

According to a mode of operation, the step of moving comprises the step of retracting the tip protector 601 along the shaft 611.

According to a mode of operation, the step of moving comprises the step of advancing the tip protector 601 along the shaft 611 towards the instrument tip 612.

According to a mode of operation, the method comprises the step of covering the instrument tip 612 by means of said tip protector 601. Thereby the articulated instrument tip 612 is received within the cavity of the housing 602 and the at least one abutment surfaces 609', 609", 609'", 609"" exerts said constraining action on the instrument tip 612, locking at least one, and preferably all the degrees of freedom of the articulated instrument tip 612.

According to a mode of operation, the method comprises the step of constraining the articulated instrument tip 612 in a predefined configuration.

According to a mode of operation, the step of constraining comprises constraining the articulated instrument tip 612 in a straight configuration aligned to the longitudinal direction X-X of the shaft 611.

According to a preferred mode of operation, the method is performed by means of an assembly 600 according to any one of the embodiments described above.

In the following will be described a method for constraining an articulated instrument tip 612 by means of a tip protector 601.

A method for constraining an articulated instrument tip 612 comprises the following steps:

- positioning a tip protector 601 having a tip housing 602 comprising at least one tip abutment surface 609', 609", 609'", 609"" onto an articulated instrument tip 612 so that the at least one tip abutment surface 609', 609", 609'", 609"" abuts against the instrument tip 612 from opposite sides of the tip 612;
- exerting a constraining action on the instrument tip 612 at least in a direction, which is transversal to the longitudinal direction X-X of the shaft 611,
- blocking at least one of the degrees of freedom of said articulated instrument tip 612.

According to a mode of operation, the step of positioning comprises the step of abutting at least a pair of opposite tip abutment surface 609', 609", 609'", 609"" against a link of the instrument tip 612 from opposite sides of the articulated tip 612.

According to a mode of operation, the step of exerting comprises the step of abutting one or more further abutment surfaces 629', 629" against the shaft 611, in order to act as reference points for the tip abutment surfaces 609', 609", 609'", 609"".

According to a mode of operation, the step of exerting comprises the step of exerting an elastic constraining action.

According to a mode of operation, the step of blocking comprises the step of mechanically locking the tip protector 601 in place.

According to a mode of operation, the step of blocking comprises the step of applying an actuation load on at least one of the degrees of freedom of the instrument tip 612.

According to a mode of operation, the method for constraining comprises one or more of the steps described above with reference to the method of repositioning.

According to a mode of operation, the method for constraining is carried out by means of a tip protector 601 and/or an assembly 600 according to any one of the embodiments described above.

Thanks to the features described above provided either together or disjointly in particular embodiments, it is allowed to respond to the above-mentioned needs providing the above cited advantages, and in particular:

- it is possible to reposition the tip protector against the shaft of the surgical instrument;
- it is possible to expose the instrument tip without for this reason requiring to reposition the surgical instrument within or away the operatory volume;
- the tip protector can be sterilized or it is disposable;

the degrees of freedom of the articulated instrument tip are freezed in a constrained configuration during any attempt to actuate said degrees of freedom;

when the articulated instrument tip is exposed out of the tip protector, i.e. when the tip protector is retracted, the articulated instrument tip is in a known pose and that may be beneficial when the surgical instrument is a slave surgical instrument of a robotic platform controlled by a mechanically ungrounded/unconstrained master input tool;

the locking mechanism may constrain the tip protector in an elastically deformed configuration, where the abutment surfaces abut against the articulated instrument tip exerting a constraining action against the instrument tip.

Those skilled in art may make many changes and adaptations to the embodiments described above or may replace elements with others, which are functionally equivalent in order to satisfy contingent needs without however departing from the scope of the appended claims.

REFERENCE LIST

600 Assembly
601 Tip protector
601' First piece of the tip protector
601" Second piece of the tip protector
602 Tip housing of the tip protector
602' First tip half-housing of the tip protector
602" Second tip half-housing of the tip protector
603 Clamping system or clamp system of the tip protector
604 Control interface of the tip protector
604' First interface surface of the tip protector
604" Second interface surface of the tip protector
605 Distal through opening of the tip protector
606 Opening size, or size of the distal through opening
607 Locking mechanism
608 Distal protective wall of the tip protector
609', 609'" Abutment surface of the tip housing
609", 609"" Abutment counter-surface of the tip housing
610 Surgical instrument
611 Shaft of the surgical instrument
612 Articulated instrument tip of the surgical instrument
613 Distal portion of the shaft
614 Proximal end of the shaft
615 Elastic tongue of the clamping system
616 Abutment portion of the clamping system
617 Sleeve of the clamping system
617' First half-pipe of the clamping system
617" Second half-pipe of the clamping system
618 Through channel of the clamping system
619 Clamping abutment surface of the clamping system
620 Robotic surgery system
621 Master console or master controller of the robotic surgery system
622 Proximal channel mouth of the through channel
622' Distal channel mouth of the through channel
623 Proximal through opening of the tip housing
624 Housing cavity of the tip housing
625 Operating volume
626 Transmission element
626' First transmission arm
626" Second transmission arm
627 Elastic element
627' First elastic arm
627" Second elastic arm
628 Root portion
629', 629" Shaft abutment surfaces of the tip protector
630 Locking tooth of the locking mechanism
631 Locking notch of the locking mechanism
632 Cam surface of the locking mechanism
633, 633', 633" End stroke portion
634 Through longitudinal passage
635 Anti-twist device, or anti-roll device
636 Chamber
637' O-ring proximal stroke end of the anti-twist device
637" O-ring distal stroke end of the anti-twist device
638 O-ring of the anti-twist device
639 Counter-clamping portion of the shaft
640 Applied action, or action
641 First portion of the shaft
642 Second portion of the shaft
643, 644, 645, 646 Links of the surgical instrument
647, 647', 648, Actuation cables of the surgical instrument, or tendons
648', 649, 649'
X-X Longitudinal direction
R-R Radial direction
C-C Circumferential direction
x-x Centerline of the tip protector
X1 Direction of retraction
X2 Direction of advance
P Pitch degree of freedom of the instrument tip
Y Yaw degree of freedom of the instrument tip
G Grip degree of freedom of the instrument tip

The invention claimed is:

1. A surgical instrument and tip protector assembly comprising:

a tip protector; and the surgical instrument having a shaft extending along a longitudinal direction and an articulated instrument tip at a distal portion of the shaft, wherein the articulated instrument tip is articulated with respect to the shaft defining at least one degree of freedom;

wherein said tip protector comprises:

a tip housing for releasably receiving the articulated instrument tip;

a clamp system configured to grip a portion of the shaft to position the tip protector; and a distal through opening at or near the distal end of the tip housing;

wherein:

said distal through opening has an adjustable opening size, so that said distal through opening can be adjusted in such way to become a through opening for at least the instrument tip, thereby making the tip protector repositionable at various locations along the shaft;

said tip protector is fitted on the shaft of the surgical instrument; and said tip housing comprises at least one tip abutment surface, wherein the at least one tip abutment surface at least partially defines the distal through opening, wherein the surgical instrument and tip protector assembly further comprises a control interface for controlling the adjustment of the opening size of said distal through opening, wherein, when the articulated instrument tip is received in the tip housing, the at least one tip abutment surface abuts against the articulated instrument tip from opposite sides thereof, and the at least one tip abutment surface exerts a constraining action that positions and orients the articulated instrument tip in a predetermined configuration and blocks at least one of the degrees of freedom of said articulated instrument tip, including preventing movement with respect to the blocked at least one of the degrees of freedom of said articulated instrument tip.

2. The assembly according to claim 1, wherein said at least one tip abutment surface is configured to block each and all the degrees of freedom of said articulated instrument tip, so that when said articulated tip is housed within a cavity of the tip housing of the tip protector in the predetermined configuration, said constraining action exerted by the at least one tip abutment surface blocks each and all the degrees of freedom of the articulated instrument tip.

3. The assembly according to claim 1, wherein said at least one tip abutment surface is connected to at least one elastic element so that said constraining action is an elastic constraining action, and wherein said constraining action blocks at least one of the degrees of freedom of said articulated instrument tip even when said at least one of the degrees of freedom is actuated.

4. The assembly according to claim 1, wherein the tip protector comprises one or more further abutment surfaces suitable to abut against the instrument shaft of the surgical instrument, with the purpose of acting as a reference for exerting said constraining action on the articulated instrument tip.

5. The assembly according to claim 1, wherein said at least one tip abutment surface is connected to at least one elastic element so that said constraining action is an elastic constraining action.

6. The assembly according to claim 1, wherein said at least one tip abutment surface is further configured to abut against the articulated instrument tip in the longitudinal direction.

7. The assembly according to claim 1, comprising a locking mechanism for temporarily limiting the opening size of the distal through opening to within a predefined size opening value, which prevents the articulated instrument tip from passing through the distal through opening of the tip housing with the purpose of strengthening said constraining action.

8. The assembly according to claim 1, wherein said control interface comprises at least two opposite interface surfaces located opposite one another with respect to the tip housing, wherein said tip protector is made of two pieces integrally fixed to one another so that elastic arms elastically bias the respective opposite interface surfaces to protrude radially away from a centerline of the tip protector, and wherein each interface surface is connected to a respective tip half-housing by means of a respective transmission arm, and wherein the tip half-housings together define said distal through opening.

9. The assembly according to claim 1, wherein said clamping system comprises an anti-twist device designed to avoid relative rotation about the longitudinal direction of the tip protector with respect to the instrument shaft.

10. The assembly according to claim 1, wherein the articulated instrument tip has at least one degree of freedom of grip, wherein said constraining action exerted by said at least one abutment surface constrains the degree of freedom of grip in the predefined configuration.

11. The assembly according to claim 1, wherein the articulated instrument tip has at least one pitch degree of freedom and yaw degree of freedom, wherein said constraining action exerted by said at least one abutment surface constrains at least one of the pitch degree of freedom or the yaw degree of freedom of the articulated instrument tip in the predefined configuration.

12. The assembly according to claim 1, wherein said predefined configuration is a straight configuration aligned to the longitudinal direction of the instrument shaft, so that said constraining action exerted by said at least one abutment surface constrains the articulated instrument tip in a straight configuration aligned to the longitudinal direction of the instrument shaft.

13. The assembly according to claim 1, wherein said surgical instrument comprises one or more tendons for articulating said one or more degree of freedom of the articulated instrument tip; wherein said constraining action exerted by the at least one abutment surface blocks at least one of the degrees of freedom of said articulated instrument tip even when said one or more of said tendons apply a traction load directed to actuate at least one of the degrees of freedom of said articulated instrument tip.

14. The assembly according to claim 5, wherein said elastic constraining action is a self-centering constraining action.

15. The assembly of claim 1, wherein the opening size of the distal through opening is elastically adjustable.

16. The assembly of claim 1, wherein said tip protector is made of two pieces, each of said two pieces being a rigid body comprising at least one elastically flexible part.

17. The assembly according to claim 6, wherein the constraining action exerted by the at least one abutment surface further prevents movement with respect to a translational degree of freedom of the articulated instrument tip.

18. The assembly according to claim 1, wherein said tip housing comprises at least a pair of tip abutment surfaces configured to abut against the articulated instrument tip from opposite sides of the instrument tip in a direction which is transverse to the longitudinal direction of the shaft, and wherein said tip protector is a clip having the opening size of the distal through opening elastically adjustable and the abutment surfaces elastically preloaded in closure toward each other.

19. The assembly according to claim 1, wherein the opening size of the distal through opening is adjustable and settable:

in an abutment configuration in which said tip abutment surface abuts against said articulated instrument tip when the articulated instrument tip is received within the tip housing, and in a pass-through configuration in which at least said articulated instrument tip passes through said distal through opening, wherein said control interface is connected to at least one transmission element that is in turn connected to at least one portion of the tip housing, so that the at least one transmission element transmits a control action from the control interface to the tip housing for adjusting the distal through opening of the tip protector, wherein said control interface comprises at least two opposite interface surfaces located opposite one another with respect to the tip housing, wherein at least one of the at least two interface surfaces is associated with an elastic element, so that the elastic element biases said at least one of the at least two interface surfaces towards a predefined position and determines the opening size of the distal through opening to assume said abutment configuration, wherein the at least two opposite interface surfaces are configured to be pressed towards one another with manual pressure applied by fingers of an operator, and wherein the pressure manually applied onto said two opposite interface surfaces determines the elastic deformation of the at least one elastic element and at the same time displaces the at least one portion of the tip housing by means of said at least one respective transmission element adjusting the opening size of the distal through opening towards said pass-through configuration.

20. The assembly according to claim 1, wherein by applying a manual action onto said control interface the opening size of said distal through opening is adjustable, and wherein, when the articulated instrument tip is received in the tip housing and when the manual action onto said control interface is released, the at least one tip abutment surface abuts against the articulated instrument tip from opposite sides thereof, and the at least one tip abutment surface exerts said constraining action.

21. A method for constraining an articulated instrument tip of a surgical instrument with a tip protector, the surgical instrument having a shaft extending along a longitudinal direction and wherein said articulated instrument tip is at a distal portion of the shaft and is articulated with respect to the shaft defining at least one degree of freedom, the tip protector having a tip housing comprising at least one tip abutment surface and a distal through opening, the at least one tip abutment surface at least partially defining the distal through opening, the method comprises the following steps:

positioning the tip protector against a first portion of the shaft;

applying an action onto an interface of the tip protector to increase an opening size of the distal through opening of said tip protector, thereby the distal through opening becomes a through passage for at least the articulated instrument tip;

moving the tip protector along the shaft; and repositioning a tip protector along the shaft in a position where the articulated instrument tip is received within the tip housing, wherein the step of repositioning involves a step of releasing the action applied onto the interface of the tip protector, thereby;

abutting the at least one tip abutment surface of the tip protector against opposite sides of the articulated instrument tip in a direction, which is transversal to the longitudinal direction;

exerting, by the at least one abutment surface, a constraining action on the articulated instrument tip, the constraining action positioning and orienting the articulated instrument tip in a predetermined configuration; and blocking, via the constraining action, at least one degree of freedom of the articulated instrument tip, comprising preventing any movement with respect to the blocked degree of freedom of the articulated instrument tip.

22. The method according to claim 21, wherein the action applied onto the interface of the tip protector is a manual action.

* * * * *